(12) United States Patent
Nakanishi et al.

(10) Patent No.: US 7,138,490 B2
(45) Date of Patent: Nov. 21, 2006

(54) BLOCK COPOLYMER REDUCED IN IMPURITY CONTENT, POLYMERIC CARRIER, PHARMACEUTICAL PREPARATIONS IN POLYMERIC FORM AND PROCESS FOR THE PREPARATION OF THE SAME

(75) Inventors: Takeshi Nakanishi, Kamagaya (JP); Kazuhisa Shimizu, Maebashi (JP); Ryuji Uehara, Takasaki (JP); Masanobu Suzuki, Saitama (JP)

(73) Assignees: Nippon Kayaku Kabushiki Kaisha, Tokyo (JP); Yasuhisa Sakurai, Tokyo (JP)

( * ) Notice: Subject to any disclaimer, the term of this patent is extended or adjusted under 35 U.S.C. 154(b) by 0 days.

(21) Appl. No.: 10/481,347

(22) PCT Filed: Jun. 19, 2002

(86) PCT No.: PCT/JP02/06112

§ 371 (c)(1),
(2), (4) Date: Mar. 26, 2004

(87) PCT Pub. No.: WO03/000771

PCT Pub. Date: Jan. 3, 2003

(65) Prior Publication Data

US 2004/0151690 A1   Aug. 5, 2004

(30) Foreign Application Priority Data

Jun. 20, 2001 (JP) ............................. 2001-187175
Jun. 20, 2001 (JP) ............................. 2001-187176

(51) Int. Cl.
*C07K 1/107* (2006.01)
*C07K 1/00* (2006.01)
*C07K 1/14* (2006.01)
*C07K 2/00* (2006.01)
*A61K 38/00* (2006.01)
*A61K 38/02* (2006.01)

(52) U.S. Cl. ............... 530/345; 530/300; 530/333; 530/335; 530/344; 514/2

(58) Field of Classification Search ............... 530/300, 530/350
See application file for complete search history.

(56) References Cited

U.S. PATENT DOCUMENTS 5,412,072 A   5/1995  Sakurai et al. ............. 530/322
5,693,751 A * 12/1997  Sakurai et al. ............. 530/322
6,080,396 A *  6/2000  Yokoyama et al. ......... 424/78.08

FOREIGN PATENT DOCUMENTS

| EP | 0 397 307 | | 11/1990 |
|---|---|---|---|
| JP | 2-300133 | | 12/1990 |
| JP | 05124969 A | * | 5/1993 |
| JP | 6-206832 | | 7/1994 |
| JP | 6206815 | | 7/1994 |
| JP | 06206832 A | * | 7/1994 |

OTHER PUBLICATIONS

English Translation JP 05124969 A, 9 pages.*
English Translation JP 06206832 A, 8 pages.*
M. Yokoyama, et al. J. Controlled Rel. (1990) 11, pp. 269-278.*
M. Yokoyama, et al. Drug Delivery (1993) 1, pp. 11-19.*
M. Yokoyama, et al. Cancer Res. (1991), 51, pp. 3229-3236.*
M. Yokoyama, et al. J. controlled Rel. (1996) 39, 351-6.*
The Communication (Supplemental European Search Report) dated Aug. 17, 2004.
The International Search Report dated Oct. 8, 2002.
The Russian communication dated Oct. 28, 2005, together with an English translation.
The Chinese Communication dated Jul. 8, 2005, together with an English translation (Chinese communication is a First Office Action in corresponding to Chinese application No. 02812284.4 filed Jun. 19, 2002; Applicant: Nippon Kayaku Kabushiki Kaisha; "Block Copolymer Reduced in Impurity Content, Polymeric Carrier, Pharmaceutical Preparations In..".

* cited by examiner

*Primary Examiner*—Cecilia J. Tsang
*Assistant Examiner*—Andrew D. Kosar
(74) *Attorney, Agent, or Firm*—Nields & Lemack

(57) ABSTRACT

A process for purification which permits satisfactory removal of impurities from a block copolymer consisting essentially of polyethylene glycols and poly(acidic amino acid) and is suitable for the production of a polymeric carrier having a pharmaceutically acceptable purity; a process for producing such a polymeric carrier; a block copolymer reduced in impurity content; a polymeric carrier as described above; pharmaceutical preparations in polymeric form, produced by the use of the carrier; and a method of subjecting polyethylene glycols and poly(acidic amino acids)—which are impurities contained in the block copolymer—to treatment with either an ion-exchange resin or a partition/absorption resin and then determining the quantities of them with a gel filtration column.

5 Claims, No Drawings

BLOCK COPOLYMER REDUCED IN IMPURITY CONTENT, POLYMERIC CARRIER, PHARMACEUTICAL PREPARATIONS IN POLYMERIC FORM AND PROCESS FOR THE PREPARATION OF THE SAME

FIELD OF THE INVENTION

The present invention relates to a high-purity block copolymer that is able to be used as a carrier upon transporting a medicine or the like, a polymeric carrier that is formed by condensing the block copolymer with an anthracycline anticancer agent and used as a medicine carrier, polymeric pharmaceutical preparations formed by the polymeric carrier, and a manufacturing method thereof. Moreover, the present invention also relates to a quantitative determination method for impurities contained in the block copolymer.

BACKGROUND ART

There has been known an approach in which, by using a polymeric carrier that forms a micelle, a medicine, genes and the like are transported to a target place in a living organism; however, with respect to the block copolymer used for this purpose, impurities have not been sufficiently removed therefrom.

Conventionally, refining processes of the synthetic high molecular compound such as a block copolymer have been carried out by using a method such as a dialysis operation, an ultrafiltration operation and a precipitating operation.

In the refining methods of the dialysis operation and ultrafiltration operation, separating and refining processes are carried out based upon a difference in molecular weights. In general, dialysis membranes and ultrafiltration films are classified into groups depending on the maximum molecular weight that is allowed to permeate; however, there are great variations in precision of molecular weights of fraction. Consequently, in the methods for refining the synthetic high molecular compound such as a block copolymer through the dialysis operation and the ultrafiltration operation, it is not possible to carry out sufficient refining processes in the case when there is not a great difference between the molecular weight of a target synthetic high molecular compound and the molecular weight of impurities. Moreover, these methods are not suitable for industrial use, and are used as refining methods in laboratories in most cases.

In contrast, the refining method using a precipitating process has been widely used as a method that is also applicable to industrial use. In this method, by using a difference in solubility to a solvent, impurities are removed so as to carry out refining processes, and this method is superior in removing low-molecular-weight components from a synthetic high molecular compound such as a block copolymer. However, in the case of impurities having greater molecular weights such as polyethylene glycols and poly(acidic amino acids), there is only a small difference in solubility to a solvent between the synthetic high molecular compound such as a block copolymer and the impurities, with the result that the high molecular compound such as a block copolymer is not sufficiently refined through the precipitating process.

As described above, impurities having great molecular weights, contained in a block copolymer, have not been sufficiently removed, and a refining method, which is suitably used for obtaining a block copolymer that is also applicable to pharmaceutical preparations and the like, has not been known.

Moreover, with respect to a micelle-forming block copolymer having amphipathic property, the conventional method for quantitatively determining impurities in the block copolymer has failed to provide sufficient analysis results.

In the conventional method, the synthetic high molecular compound such as a block copolymer is dissolved in a solvent, and analyzed by using a high speed liquid chromatography to which a gel permeation column is connected (gel permeation chromatography: GPC).

However, in the case when there is only a small difference in molecular weights among the block copolymer and impurities contained therein, it is difficult to separate them with clear peaks, failing to provide sufficient performance as quantitative determination method for impurities.

Moreover, even in the case when there is a sufficient difference in molecular weights among them, if the quantity of impurities is small, it is not possible to obtain clear peaks. This is because since the gel permeation separation mechanism utilizes molecular diffusion, a peak tends to spread on the chromatogram to cause insufficient peak heights with respect to a component that is small in quantity. Consequently, the conventional method has failed to provide a quantitative determination method with sufficient performance.

Furthermore, since the conventional method separates and quantitatively determines a main component and impurities depending upon only the difference in molecular weights, no qualitative information, such as structures and provenance of impurities, is obtained.

DISCLOSURE OF THE INVENTION

The inventors of the present invention have studied hard to solve the above-mentioned problems, and devised the present invention.

In other words, the present invention relates to:

1) A block copolymer of polyethylene glycols and poly (acidic amino acid), or a salt thereof, wherein impurities have a content of not more than 10% by weight.

2) The block copolymer or the salt thereof according to 1), wherein the impurities are polyethylene glycols and poly (acidic amino acids).

3) The block copolymer or the salt thereof according to 1) or 2), wherein the poly(acidic amino acid) is polyaspartic acid.

4) The block copolymer or the salt thereof according to 1) or 2), wherein the block copolymer is a copolymer represented by formula (1):

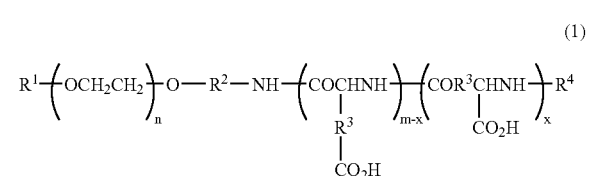

(wherein, $R^1$ represents a hydrogen atom or a lower alkyl group, $R^2$ represents a bonding group, $R^3$ represents a methylene group or an ethylene group and $R^4$ represents a hydrogen atom or a protective group of an amino group, and n is an integer of 5 to 1000, m is an integer of 2 to 300 and x is an integer of 0 to 300; however, x is not greater than m.)

5) The block copolymer or the salt thereof according to 4), wherein $R^1$ represents an alkyl group having 1 to 5 carbon atoms, $R^2$ represents an alkylene group having 1 to 5 carbon atoms, $R^3$ represents a methylene group or an ethylene group and $R^4$ represents a hydrogen atom or an acyl group having 1 to 5 carbon atoms, and n is an integer of 5 to 1000, m is an integer of 2 to 300 and x is an integer of 0 to 300, however, x is not greater than m in formula (1).

6) The block copolymer or the salt thereof according to 4) wherein $R^1$ represents a methyl group, $R^2$ represents a trimethylene group, $R^3$ represents a methylene group and $R^4$ represents an acetyl group, and n is an integer of 20 to 500, m is an integer of 10 to 100 and x is an integer of 0 to 100, however, x is not greater than m in formula (1).

7) A manufacturing method of the block copolymer or the salt thereof according to any one of 1) to 6), wherein a polyethylene glycol derivative is refined by an ion exchange resin to prepare a block copolymer, and after the protective group has been removed, if necessary, a refining process is carried out by using a partition/adsorption resin.

8) A polymeric carrier, wherein the poly(acidic amino acid) of the block copolymer according to anyone of 1) to 6) is condensed with an anthracycline anticancer agent residue.

9) The polymeric carrier according to 8), wherein the condensation between the poly(acidic amino acid) and the anthracycline anticancer agent residue is a condensation between a side-chain carboxylic acid of the poly(acidic amino acid) and the anthracycline anticancer agent residue.

10) The polymeric carrier according to 8) or 9), wherein the anthracycline anticancer agent residue is doxorubicin residue.

11) The polymeric carrier according to 8) or 9), wherein the anthracycline anticancer agent residue in the poly(acidic amino acid) has a bonding rate of 30 to 55%.

12) A manufacturing method of the polymeric carrier according to any one of 8) to 11), wherein, after a condensation compound between the block copolymer described in any one of 1) to 6) and a reaction assistant has been separated, the condensation compound is allowed to react with an anthracycline anticancer agent.

13) The manufacturing method of the polymeric carrier according to 12), wherein the anthracycline anticancer agent is doxorubicin or a salt thereof.

14) A polymeric pharmaceutical preparation containing a block copolymer-medicine complex in which an anthracycline anticancer agent is contained in an inner core of a micelle formed by the polymeric carrier according to any one of 8) to 11).

15) The polymeric pharmaceutical preparation according to 14), wherein the anthracycline anticancer agent is doxorubicin or a salt thereof.

16) The polymeric pharmaceutical preparation according to 14) or 15), wherein the block copolymer-medicine complex is contained in a form of a freeze-dried matter.

17) A quantitative determination method of impurities contained in the block copolymer of polyethylene glycols and poly(acidic amino acid) according to 1), comprising the steps of:
dissolving the block copolymer in a solvent;
subjecting the solution to a resin treatment; and
subjecting the treated solution to a high speed liquid chromatography treatment using a gel permeation column.

18) The quantitative determination method according to 17), wherein the solvent is water that is allowed to contain an organic solvent that is mixed with water, the resin is an ion exchange resin, and the impurities are polyethylene glycols.

19) The quantitative determination method according to 17), wherein the solvent is water that is allowed to contain an organic solvent that is mixed with water, the resin is a partition/adsorption resin that adsorbs a compound having an ether bond, and the impurities are poly(acidic amino acids).

BEST MODE FOR CARRYING OUT THE INVENTION

The following description will discuss the present invention in detail.

A first aspect of the present invention relates to a block copolymer of polyethylene glycols and poly(acidic amino acid), or a salt thereof, in which impurities have a content of not more than 10% by weight. As a result of analyses of the impurities contained in the block copolymer, it has been found that the impurities consist of polyethylene glycols and poly (acidic amino acid), that is, polyamino acid having carboxylic acid on its side chain. Examples of the polyethylene glycols include polyethylene glycol, and one-terminal alkoxy polyethylene glycol. Examples of poly(acidic amino acid) include polyglutamic acid and polyaspartic acid.

In the present invention, with respect to the poly(acidic amino acid) in the block copolymer of polyethylene glycols and poly(acidic amino acid), examples thereof include a polymer of α- and/or β-amino acid having a carboxylic group on its side chain, preferably, polyglutamic acid or polyaspartic acid, and with respect to the block copolymer, examples thereof include block copolymers represented by the above-mentioned formula (1) or (2) or salts thereof.

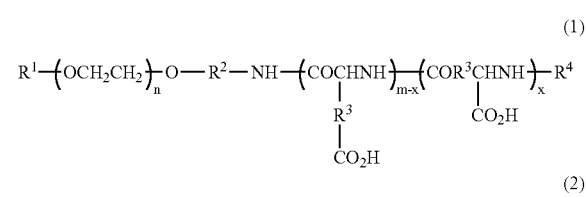

(1)

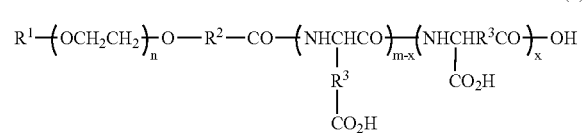

(2)

(wherein, $R^1$ represents a hydrogen atom or a lower alkyl group, $R^2$ represents a bonding group, $R^3$ represents a methylene group or an ethylene group and $R^4$ represents a hydrogen atom or a protective group of an amino group, and n is an integer of 5 to 1000, m is an integer of 2 to 300 and x is an integer of 0 to 300; however, x is not greater than m.)

Here, examples of $R^1$ include a hydrogen atom or a lower alkyl group, and a lower alkyl group is preferably used, and specific examples thereof include a methyl group, an ethyl group, an n-propyl group and an i-propyl group; in particular, a methyl group is more preferably used. With respect to a bonding group of $R^2$, examples thereof include a hydrocarbon group that may have a branch, and an alkylene group is preferably used, and specific examples thereof include an ethylene group, a trimethylene group and a tetramethylene group; in particular, an ethylene group and a trimethylene group are more preferably used. With respect to $R^3$, amethylene group or an ethylene group is used, and a methylene group is more preferably used.

With respect to $R^4$, a hydrogen atom or a protective group of an amino group is used, and, with respect to the protective group of an amino group, not particularly limited, any group may be used as long as it is a normally used protective group of an amino group; in particular, a lower acyl group is preferably used, and specific examples thereof include a formyl group, an acetyl group, a propionyl group and a butyroyl group, and an acetyl group is more preferably used. Here, n is an integer of 5 to 1000, more preferably, 20 to 500, most preferably, 80 to 300, m is an integer of 2 to 300, more preferably, 10 to 100, most preferably, 20 to 50, and x is an integer of 0 to 300, more preferably, 0 to 100, most preferably, 0 to 50; however, x is not greater than m.

With respect to the salt of a block copolymer in the present invention, examples thereof include an alkali metal salt, an alkali earth metal salt, an ammonium salt and an organic ammonium salt, and preferable examples are a sodium salt, a potassium salt, a calcium salt, an ammonium salt and a triethyl ammonium salt.

It is considered that impurities contained in the block copolymer do not form a micelle and have no functions for serving as a polymeric carrier of a medicine, a gene or the like; therefore, for the purpose of medical use, the content of the impurities is preferably reduced to not more than 10%, more preferably, not more than 5%.

Moreover, a second aspect of the present invention relates to a manufacturing method of a block copolymer of polyethylene glycols and poly(acidic amino acid), or a salt thereof, in which polyethylene glycols are refined by an ion exchange resin followed by forming a block copolymer with poly(acidic amino acid), and after removing a protective group therefrom, if necessary, the block copolymer is refined by using a partition/adsorption resin. With respect to the block copolymer of polyethylene glycols and poly(acidic amino acid), the same block copolymer as the above-mentioned block copolymer of polyethylene glycols and poly (acidic amino acid) is preferably used. In the case when the block copolymer is protected by a protective group, with respect to the protective group, although not particularly limited as long as it normally protects a carboxylic group in a side chain of the acidic amino acid, examples thereof include an ester with a lower alcohol and an ester with an aryl-group substituted lower alcohol that may have a substituent. Specific examples are methyl ester, ethyl ester, propyl ester, butyl ester, benzyl ester, phenetyl ester, p-methoxybenzyl ester and p-nitrobenzyl ester. With respect to the method for removing the protective group, an appropriate method is selected from normally-used methods depending on the protective group, and, for example, a hydrolytic method by acid or alkali and a hydrogenolysis method using a catalyst or the like may be used.

With respect to the block copolymer of polyethylene glycols and poly(acidic amino acid) of the present invention that is reduced in impurity content, the following description will discuss the refining method of, for example, a compound represented by formula (1).

With respect to the synthesizing method of the block copolymer, various methods are proposed; and, for example, Japanese Patent Application Laid-Open No. 6-206832 has disclosed a method in which a material, obtained by modifying a hydroxide group terminal of one-terminal methoxy polyethylene glycol, is subjected to a polymerization reaction with aspartic acid derivatives, followed by protecting the amino group, then an ester bond being hydrolyzed, so that a block copolymer is produced; however, there have not been known any refining methods for obtaining the block copolymer with high purity.

The modifying process of the hydroxide group terminal of one-terminal methoxy polyethylene glycol can be carried out by methods using reactions that have been known in the corresponding industrial art, and, for example, the following methods have been proposed: a method in which ethylene imine or the like is allowed to react, a method in which, after acrylonitrile, methacrylonitrile or the like has been subjected to Michel addition process, the nitrile group is reduced to be converted to an amino group, a method in which, after the hydroxide group has been substituted to a halogen group, this is allowed to react with alcohol amine such as ethanol amine, and a method in which the hydroxide group is directly converted to a nitrile group, and then reduced to be converted to an amino group.

The polyethylene glycol the terminal of which is modified to an amino group includes one-terminal polyethylene glycols having incomplete modification, that is, for example, one-terminal polyethylene glycol having a terminal of a hydroxide group and one-terminal polyethylene glycol having a terminal to which acrylonitrile is added.

These polyethylene glycols having incomplete modification can be removed in a separate manner by using an ion exchange material having an acidic functional group. Although not particularly limited as long as it has anacidic functional group, examples of the ion exchange material to be used include: Diaion SKIB (made by Mitsubishi Chemical Corporation), Diaion PK-216 (made by Mitsubishi Chemical Corporation), Diaion WK-10 (made by Mitsubishi Chemical Corporation), Diaion WK20 (made by Mitsubishi Chemical Corporation), Amber lite 120B (made by Rohm and Haas Japan Co.), Amber lite 200C (made by Rohm and Haas Japan Co.), Amber lite IRC-50 (made by Rohm and Haas Japan Co.), Amber lite IRC-76 (made by Rohm and Haas Japan Co.) and Dowex50W (made by Dow Chemical Corp.), which serve as ion exchange resins; and also include SP-Sephadex C-25 (made by Pharmacia Biotech), SP-Sephadex C-50 (made by Pharmacia Biotech), CM-Sephadex C-25 (made by Pharmacia Biotech), CM-Sephadex C-50 (made by Pharmacia Biotech), SP-Toyopearl 550 (made by Toso K.K.), SP-Toyopearl 650 (made by Toso K.K.), CM-Sephadex 550 (made by Pharmacia) and CM-Sephadex 650 (made by Pharmacia), which serves as ion exchange gel, and in particular, SP-Toyopearl 650 and CM-Sephadex 650 are preferably used.

The method for refining the resulting polyethylene glycol may be either of a batch method and a column method; and the column method is more preferably used. In other words, one-terminal-methoxy polyethylene glycol having a modified terminal is dissolved in a solvent. The solvent to be used is not particularly limited as long as it is applicable to ion exchange process, and water or a mixed solvent of water/organic solvent, such as water/methanol and water/acetonitrile, is preferably used. Successively, the resulting solution is allowed to pass through a column in which the above-mentioned ion exchange material reproduced into an $H^+$ form has been charged, and the column is then washed with water or a mixed solvent of water/organic solvent so that polyethylene glycols that have been incompletely modified are removed therefrom. Thereafter, one-terminal methoxy polyethylene glycol with the terminal modified to an amino group, which has been adsorbed, is eluted by using a solvent with a basic substance added thereto, such as aqueous ammonia or a mixed solvent of aqueous ammonia/organic solvent. The solution thus eluted is subjected to appropriate processes, such as a condensing process or a freezing and drying process, so that one-terminal methoxy polyethylene glycol with the terminal modified to an amino group, which has high purity, is obtained.

Next, the one-terminal methoxy polyethylene glycol with the terminal modified to an amino group is allowed to react with, for example, an N-carboxylic anhydride of amino acid in which a carboxylic group on a side chain has been protected so that a block copolymer is synthesized, and, if necessary, the amino group on the terminal is then acetylated by acetic anhydride or the like. Thereafter, if necessary, the protected group on the side chain is deprotected so that a polyethylene glycol-poly(acidic amino acid) block copolymer is obtained.

The polyethylene glycol-poly(acidic amino acid) block copolymer, thus obtained, contains poly(acidic amino acid) as an impurity; however, this can be refined by using a partition/adsorption resin. With respect to the partition/adsorption resin, examples thereof include silica gel, silicate powder, silica gel modified by hydrocarbon and styrene/divinylbenzene resin, and styrene/divinylbenzene resin is preferably used; further, more preferably, HP-20 SS (made by Mitsubishi Chemical Corporation) is used.

The method for refining the resulting polyethylene glycol-poly(acidic amino acid) copolymer may be either of a batch method and a column method; and the column method is more preferably used. In other words, the polyethylene glycol-poly(acidic amino acid) block copolymer is dissolved in a solvent. The solvent to be used is not particularly limited as long as it has a sufficient basic property for dissociating the poly(acidic amino acid), and is applicable to the partition/adsorption resin; and preferable examples include an aqueous solution of alkali metal hydroxide or a mixed solution of aqueous solution of alkali metal hydroxide and organic solvent, such as aqueous solution of sodium hydroxide/methanol and aqueous solution of sodium hydroxide/acetonitrile. The solution of polyethylene glycol-poly(acidic amino acid) block copolymer dissolved in the solvent is allowed to pass through a column in which a partition/adsorption resin has been charged, and an aqueous solution of sodium hydroxide or a mixed solvent of aqueous solution of sodium hydroxide/organic solvent is then allowed to pass through the column so that the poly (acidic amino acid) is removed. Thereafter, the adsorbed polyethylene glycol-poly (acidic amino acid) block copolymer is eluted by using a less polar solvent, such as a mixed solvent of water/organic solvent with an increased ratio of the organic solvent. The solution thus eluted is subjected to appropriate post-processes, such as a condensing process, a freezing and drying process or precipitation, so that a polyethylene glycol-poly (acidic amino acid) block copolymer having high purity is obtained.

A third aspect of the present invention relates to a polymeric carrier that is obtained by condensing the refined block copolymer of polyethylene glycols and poly(acidic amino acid), together with anthracycline anticancer agent. With respect to the polymeric carrier, a high molecular compound, represented by the following formula (3) or (4), is proposed. The present invention also includes salts thereof.

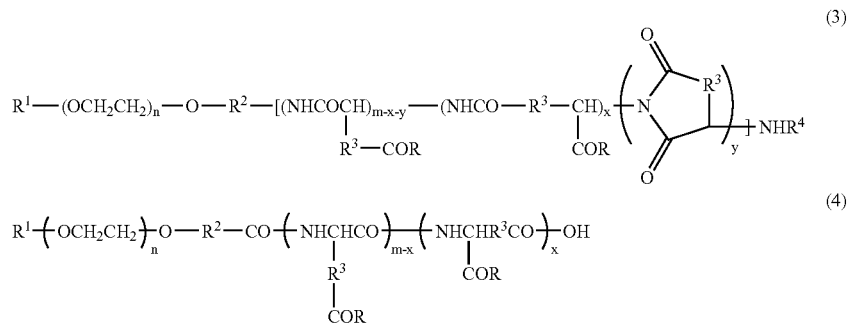

(wherein, R represents a hydroxide group or an anthracycline anticancer agent residue, $R^1$ represents a hydrogen atom or a lower alkyl group, $R^2$ represents a bonding group, $R^3$ represents a methylene group or an ethylene group and $R^4$ represents a hydrogen atom or a protective group of an amino group, and n is an integer of 5 to 1000, m is an integer of 2 to 300 and x+y is an integer of 0 to 300; however, x+y is not greater than m.)

With respect to R in the compound represented by formula (3) or (4) in the present invention, examples thereof include a hydroxide group or an anthracycline anticancer agent residue. In the poly(acidic amino acid) portion of the block copolymer, the order of bonding of the respective constituent parts is not particularly limited, and may be randomly set or regularly set. The bonding mode between the side chain carboxylic acid residue of the poly(acidic amino acid) of the block copolymer and the anthracycline anticancer agent residue is not particularly limited, and the amide bond to the amino group of the anthracycline anticancer agent residue is preferably used. In particular, the amide bond formed by a primary amino group of the amino sugar portion of the anthracycline anticancer agent residue is preferably used. The rate of the anthracycline anticancer agent being bonded to the side chain carboxylic acid residue of the poly(acidic amino acid) portion is 1 to 100%, and when the capability of forming a micelle is taken into consideration, the rate is preferably set in a range of 10 to 60%, more preferably, 30 to 55%. Examples of the anthracycline anticancer agent residue include residues such as daunorubicin, doxorubicin, acrarubicin, epirubicin and pyrarubicin, and doxorubicin residues are more preferably used.

$R^1$, $R^2$, $R^3$, $R^4$, n and m are preferably set in the same range as described earlier.

Here, x+y is an integer of 0 to 300, preferably, 0 to 100, more preferably, 0 to 50, and x and y may be any values including 0 as long as each of them is an integer that satisfies the above-mentioned conditions.

Moreover, a fourth aspect of the present invention relates to a manufacturing method for a polymeric carrier that is obtained through processes in which: the refined block copolymer of polyethylene glycols and poly(acidic amino acid) is condensed with a reaction assistant, and after the condensation compound has been separated, this is allowed to react with an anthracycline anticancer agent. The polymeric carrier is obtained by a method disclosed in the pamphlet of International Publication No. WO97/12895, that is, a method in which a block copolymer and an anthracycline anticancer agent are condensed by using a carbodiimide-type dehydration condensation agent; however, at this time, acylisourea, which is an active intermediate, is transferred by intramolecular rearrangement to produce acyl urea as a by-product, resulting in a polymeric carrier to which acyl urea is added. Here, by separating the condensation compound between the block copolymer and the reaction assistant, it becomes possible to reduce the by-product acyl urea, and consequently to provide a polymeric carrier with less acyl urea added thereto. The temperature of the injection port of the gas chromatography is set to a sufficiently high level, then the quantity of by-product acyl urea added thereto is quantitatively determined by measuring the isocyanate derivatives that have been thermally decomposed from the acyl urea.

The following description will explain the above-mentioned manufacturing method more specifically: The refined block copolymer is dissolved in an organic solvent, and to this are added a dehydration condensation agent and a reaction assistant so that a reaction takes place, and alkyl urea derivatives, generated through the reaction, are filtered so that an active ester material is separated from the filtrate. Successively, after an anthracycline anticancer agent or the salt thereof has been added to the resulting active ester material in an organic solvent, a base is added thereto, if necessary, to react them, and a polymeric carrier is isolated from the reaction solution. With respect to the organic solvent, although not particularly limited as long as the reaction material is dissolved therein, a nonaqueous polar solvent is preferably used, and examples thereof include dimethyl formamide, dimethyl acetamide and 1,3-dimethyl-2-imidazolidinone, and dimethyl formamide is more preferably used. With respect to the dehydration condensation agent to be used for condensation between the block copolymer and the reaction assistant, a condensation agent normally used for peptide synthesis is used, and such as dicyclohexyl carbodiimide (DCC) and 1-ethyl-3-(3-dimethylaminopropyl) carbodiimide (EDC) are preferably used. With respect to the reaction assistant, a reaction assistant normally used for peptide synthesis is used. Examples thereof include N-hydroxy compounds, and N-hydroxy succinimide, N-hydroxy benzotriazole and the like are preferably used. With respect to the base to be used, although not particularly limited, organic bases such as triethyl amine are preferably used. With respect to the anthracycline anticancer agent, an anthracycline-based compound that supplies the above-mentioned anthracycline anticancer agent residue is used.

Furthermore, a fifth aspect of the present invention relates to a polymeric pharmaceutical preparation that contains a block copolymer-medicine complex in which an anthracycline anticancer agent is enclosed in the inner core of a micelle formed by a polymeric carrier that is manufactured by a refined block copolymer of polyethylene glycols and poly (acidic amino acid) Examples of the anthracycline anticancer agent include compounds, such as daunorubicin, acrarubicin, epirubicin and pyrarubicin, or salts thereof, and doxorubicin or salt thereof is more preferably used. Moreover, another aspect of the present invention also relates to a polymeric pharmaceutical preparation in which the block copolymer-medicine complex is contained in the form of a freeze-dried matter. The manufacturing method of the above-mentioned polymeric pharmaceutical preparation is not particularly limited, and the method disclosed in Japanese Patent Application Laid-Open No. 7-69900, that is, a method in which a mixed solvent of dimethyl formamide and water in which the block copolymer and anthracycline anticancer agent are dissolved is subjected to a dialysis operation using a dialysis membrane and an ultrafiltration operation using an ultrafiltration film and this is frozen and dried, if necessary, may be used. Moreover, another method may be used in which the block copolymer and the anthracycline anticancer agent are dissolved in a mixed solvent of a low-boiling-point organic solvent that is mixed with water, such as ethanol, and water, and the resulting solution is condensed so as to distill the low-boiling-point organic solvent off, and frozen and dried, if necessary.

A sixth aspect of the present invention relates to a quantitative determination method in which, upon quantitative determination impurities contained in the above-mentioned block copolymer of polyethylene glycols and poly (acidic amino acid), the block copolymer is dissolved in a solvent, and the solution is subjected to a resin treatment so that the treatment solution is subjected to a high speed liquid chromatography treatment using a gel permeation column. With respect to the block copolymer of polyethylene glycols and poly(acidic amino acid) and the impurities contained in the block copolymer, examples thereof are the same as those described earlier.

In the present invention, with respect to the solvent used for dissolving the block copolymer of polyethylene glycols and poly(acidic amino acid) upon quantitatively determining polyethylene glycols contained as impurities, any desired solvent capable of dissolving the block copolymer can be used; and preferably, an aqueous solution the pH of which is adjusted by using appropriate salt, or a mixed solvent of this aqueous solution and an organic solvent, such as methanol, ethanol, acetonitrile and tetrahydrofran, is used. With respect to the salt used for adjusting the pH, normally-used salts having a buffering function may be used, and preferably, phosphates, borates, sodium hydrogencarbonate, phthalates, tris-hydrochlorides and the like are used.

Moreover, with respect to the solvent used for quantitatively determining polyamino acid contained as impurities, any desired solvent that is capable of dissolving the block copolymer of polyethylene glycols and poly(acidic amino acid) and of dissociating carboxylic acid on a side chain, upon quantitatively determining polyethylene glycols may be utilized; and preferably, an aqueous solution the pH of which is adjusted by using appropriate salt or a mixed solvent of this aqueous solution and an organic solvent, such as methanol, ethanol, acetonitrile and tetrahydrofran, is used. In order to properly dissociate the carboxylic acid on a side chain, the pH of the solvent is preferably set in a range of 5 to 13, and with respect to the salt to be used for this purpose, the above-mentioned phosphates, borates, sodium hydrogencarbonate, phthalates, tris-hydrochlorides and the like are used.

In the present invention, with respect to the resin used for processing the solution of the block copolymer upon quantitatively determining polyethylene glycols contained in the block copolymer as impurities, an ion exchange resin, which can form a counter ion to an ion dissociated group of the block copolymer, that is, an anion exchange resin, is preferably used; and not particularly limited, any ion exchange resin, such as a dialkyl amine, a trialkyl amine and a dialkyl ethanol amine, may be used as long as it has a basic functional group.

With respect to the analyzing method, either of a batch method and a column method may be used; and the column method is more preferably used.

In the column method, a method is proposed in which: to an open column is charged an ion exchange resin, such as Diaion SA10A (made by Mitsubishi Chemical Corporation), Diaion PA318 (made by Mitsubishi Chemical Corporation), Diaion SA20A (made by Mitsubishi Chemical Corporation), Diaion WA30 (made by Mitsubishi Chemical Corporation), Diaion WA10 (made by Mitsubishi Chemical Corporation), Amber lite IRA402 (made by Rohm and Haas Japan Co.), Amber lite MR904 (made by Rohm and Haas Japan Co.), Amber lite IRA410 (made by Rohm and Haas Japan Co.), Amber lite IRA93 (made by Rohm and Haas Japan Co.), Amber lite IRA68 (made by Rohm and Haas Japan Co.), and Dowex66 (made by Dow Chemical Japan Corp.); a cellulose ion exchange material, such as Cellex QAE (made by Bio-Rad Co., Ltd.), Cellex PEI (made by Bio-Rad Co., Ltd.), Cellex D (made by Bio-Rad Co., Ltd.) and Cellex DE52 (made by Bio-Rad Co., Ltd.); or a gel ion exchange material, such as QAE-Sephadex A25 (made by Pharmacia Biotech), QAE-Sephadex A50 (made by Pharmacia Biotech), DEAE-Sephadex A25 (made by Pharmacia Biotech), DEAE-Sephadex A50 (made by Pharmacia Biotech), DEAE-Separose CL-6B (made by Pharmacia Biotech) and DEAE-Bio Gel A (made by Pharmacia Biotech); or another method is proposed in which a commercial cartridge which has an ion exchange resin preliminarily charged therein, and is used for the pre-processing of the high speed liquid chromatography, such as Sep-Pak QMA (made by Waters Co., Ltd.), Sep-Pak NH2 (Waters Co., Ltd.), Bond Elut PSA (made by Barian Co., Ltd.), Bond Elut DMA (made by Barian Co., Ltd.) and Bond Elut SAX (made by Barian Co., Ltd.). Here, from the viewpoint of easiness for analysis, the method using cartridges is more preferably used. In particular, Sep-Pak QMA is more preferably used.

In a quantitative analysis for polyethylene glycols contained in the block copolymer as impurities, some of polyethylene glycols that have been subjected to the above-mentioned resin treatments, and eluted without being adsorbed to the resin are analyzed by a high speed liquid chromatography using a gel permeation column to obtain the results of the analysis. In this method, since the eluted solution can be condensed to a high concentration, it becomes possible to quantitative-analyze polyethylene glycols with high sensitivity.

In the present invention, with respect to the carrier for a gel permeation column for use in quantitative measurements for impurities, not particularly limited, any carrier can be used as long as it is used for the high speed liquid chromatography; however, depending on approximate molecular weights of impurities in the block copolymer, those carriers having appropriate exclusion limit molecular weights are used. With respect to quantitative measurements for polyethylene glycols, for example, the following carriers are used: Shodex OHpak SB-803 HQ (made by Showa Denko K.K.), Shodex OHpak SB-802.5 HQ (made by Showa Denko K.K.), Shodex OHpak SB-804 HQ (made by Showa Denko K.K.), and with respect to quantitative measurements for poly(acidic amino acids), for example, the following carriers are used: Asahipak GF-310 HQ (made by Asahi Kasei Corporation) and Asahipak GF-510 HQ (made by Asahi Kasei Corporation). In addition to these, Asahipak GS-320 HQ (made by Asahi Kasei Corporation) and Shodex OHpak Q-802 (made by Showa Denko K.K.) may also be used. With respect to the high speed liquid chromatography in the present invention, a commercial high speed liquid chromatography device can be used.

Moreover, with respect to the resin that is used for processing the solution of the block copolymer so as to carry out quantitative measurements on poly(acidic amino acids) contained in the block copolymer between polyethylene glycols and poly(acidic amino acid) of the present invention as impurities, a resin which adsorbs the block copolymer having an ether bond, that is, a partition/adsorption resin, is preferably used; and examples thereof include silica gel, silicate powder, silica gel modified by hydrocarbon and styrene/divinyl benzene resin. With respect to the silica gel modified by hydrocarbon, silica gel modified by hydrocarbon having 1 to 30 carbon atoms is preferably used, and in particular, silica gel modified by hydrocarbon having 4 to 18 carbon atoms is more preferably used.

With respect to the analyzing method, either of a batch method and a column method may be used; and the column method is more preferably used. Moreover, a column charged with a commercial partition/adsorption resin may be used, and the size thereof is desirably set. Furthermore, commercial analyzing solid-state extraction columns, such as Sep-Pak C18 (made by Waters Co., Ltd.), Sep-Pak tC18 (made by Waters Co., Ltd.), Sep-Pak C8 (made by Waters Co., Ltd.), Bond Elut C18 (made by Barian Co., Ltd.) and Bond Elut C8 (made by Barian Co., Ltd.), may also be used, and Sep-Pak C18 is more preferably used.

With respect to poly(acidic amino acids) contained in the block copolymer as impurities, quantitative measurements thereof are carried out in the following manner: the solution in which the poly(acidic amino acid) has been dissolved by such a solvent as to dissociate carboxylic acid is subjected to the above-mentioned resin treatments, and poly(acidic amino acids) which has been eluted without being adsorbed to the resin is quantitatively determined by a high speed liquid chromatography using a gel permeation column. In this method, since the eluted solution can be condensed to a high concentration, it becomes possible to quantitative-analyze poly(acidic amino acids) with high sensitivity.

By using these analyzing methods, quantities of polyethylene glycols and polyaspartic acids, which were respectively contained in the block copolymer of polyethylene glycols and polyaspartic acid obtained through the above-mentioned refining processes as well as in a conventional block copolymer of polyethylene glycols and polyaspartic acid, were measured, and the results thereof are shown below:

Quantities of impurities contained in the block copolymer

| Impurities | Not refined | Refined |
| --- | --- | --- |
| Polyethylene glycols | 6.0% by weight | 1.3% by weight |
| Polyaspartic acid | 7.5% by weight | 2.4% by weight |

EXAMPLES

The following description will discuss the present invention in detail by reference to examples. However, the present invention is not intended to be limited by these examples.

Production Example 1

Toyopearl 650 M (900 mL), reproduced into an H$^+$ form, was charged into a glass column. One-terminal-methoxy/one-terminal-3-aminopropoxy polyethylene glycol (29.97 g) (weight-average molecular weight 5287) was dissolved in 1.98 L of a 10% acetonitrile aqueous solution, and this solution was allowed to permeate through the column. After the column had been washed with 1.6 L of 10% acetonitrile aqueous solution, the column was developed by using 0.4 M aqueous ammonia containing 10% acetonitrile. Fractions containing the target compound were collected, and after having been condensed under reduced pressure, these were frozen and dried to obtain 25.71 g of purified one-terminal-methoxy/one-terminal-3-aminopropoxy polyethylene glycol.

Production Example 2

The purified one-terminal-methoxy/one-terminal-3-aminopropoxy polyethylene glycol (23.32 g), obtained in production example 1, was dissolved in 466 mL of dimethyl sulfoxide (DMSO), and heated to 35° C. To this was added 42.87 g of β-benzyl L-aspartate-N-carboxylic anhydride (BLA-NCA), and allowed to under go a reaction for 22 hours. The reaction mixture was dripped into a mixed solvent containing 3.73 L of diisopropyl ether (IPE) and 0.93 L of ethanol (EtOH), and the deposited precipitate was filtered, and washed with a mixed solution (4:1) of IPE and EtOH, followed with IPE, and then vacuum-dried so that 54.29 g (number of aspartic acid units: 29.0) of one-terminal methoxy polyethylene glycol-poly(β-benzyl L-aspartate) copolymer was obtained.

Production Example 3

The one-terminal methoxy polyethylene glycol-poly (β-benzyl L-aspartate) copolymer (52.85 g), obtained in production example 2, was dissolved in 529 mL of dimethyl formamide, and heated to 35° C. To this was added 2.50 mL of acetic anhydride, and allowed to undergo a reaction for 3 hours. The reaction mixture was dripped into a mixed solvent containing 4.76 L of diisopropyl ether (IPE) and 0.53 L of ethanol (EtOH), and the deposited precipitate was filtered, and washed with a mixed solution (9:1) of IPE and EtOH, followed with IPE, and then vacuum-dried so that 51.67 g of one-terminal-methoxy polyethylene glycol-poly (β-benzyl L-aspartate) copolymer N-acetylated compound was obtained.

Production Example 4

The one-terminal-methoxy polyethylene glycol-poly(β-benzyl L-aspartate) copolymer N-acetylated compound (50.19 g), obtained in production example 3, was allowed to react with 753 mL of acetonitrile and 2.16 L of 0.2-N sodium hydroxide solution for 5 hours. After the reaction mixture had been neutralized with 2-N hydrochloric acid, it was condensed under reduced pressure to remove acetonitrile therefrom, and then subjected to extracting processes by using 1.2 L of ethyl acetate three times. After the aqueous layer had been condensed, the amount of the solution was set to 1.3 L, and to this was further added 11 mL of 6-N sodium hydroxide to form a basic aqueous solution, and the solution was allowed to permeate through an HP-20 SS column (2 L) that had been sufficiently washed. After having been washed with a 0.01-N sodium hydroxide aqueous solution (8 L) and water (3 L), this was eluted with 50% acetonitrile-water (6 L). Fractions containing the target compound were collected, and condensed under reduced pressure, and the resulting solution was allowed to permeate through Dowex 50W8 (520 mL) that had been reproduced into an H$^+$form, and washed with 50% acetonitrile-water (1 L). The eluted solution was further condensed under reduced pressure, and then frozen and dried. The freeze-dried product thus obtained was dissolved in 320 mL of dimethyl formamide (DMF), and the resulting solution was dripped into a mixed solvent of 2.56 L of hexane and 0.64 L of ethyl acetate. The deposited precipitate was filtered, and washed with a mixed solution (4:1) of hexane and ethyl acetate, followed with hexane, and then vacuum-dried to obtain 33.20 g of one-terminal-methoxy polyethylene glycol-polyaspartic acid copolymer N-acetylated compound.

Production Example 5

The one-terminal-methoxy polyethylene glycol-polyaspartic acid copolymer N-acetylated compound (28.85 g), obtained in production example 4, was dissolved in 577 mL of dimethyl formamide, and heated to 35° C. To this were added 19.75 g of dicyclohexyl carbodiimide (DCC) and 11.01 g of N-hydroxy succinimide (HOSu), and allowed to react with these for 1 hour. The resulting dicyclohexyl urea was filtered through a cotton plug. The filtrate thus obtained was diluted with 2.3 L of ethyl acetate, and to this was then added 3.5 L of hexane. The deposited precipitate was filtered, and washed with a hexane: ethyl acetate (3:1) solution, and then vacuum-dried to obtain 33.82 g of one-terminal-methoxy polyethylene glycol-polyaspartic acid copolymer N-acetylated compound-HOSu active ester material.

Production Example 6

The one-terminal-methoxy polyethylene glycol-polyaspartic acid copolymer N-acetylated compound-HOSu active ester material (33.73 g), obtained in production example 5, was dissolved in 1.35 L of dimethyl formamide, and heated to 35° C. To this was added 26.13 g of doxorubicin hydrochloride in powder, and after having been suspended in a reaction solution, to this was further added 8.16 mL of triethyl amine and allowed to react for 1 hour. The reaction mixture was dripped in a mixed solvent containing 4.0 L of ethyl acetate and 16.0 mL of hexane, and the deposited precipitate was filtered and washed with a hexane:ethyl acetate (3:1) solution, and then vacuum-dried. Next, the resulting precipitate was suspended in 590 mL of acetonitrile, and to this was then added 1780 mL of water, and heated and stirred at 35° C. After confirming that the precipitate had been dissolved, the stirring process was continued for 1 hour, and the reaction solution was then condensed under reduced pressure to remove acetonitrile therefrom, and freeze-dried. The resulting freeze-dried product was re-dissolved in 1.074 L of dimethyl formamide, and the resulting solution was dripped in a mixed solvent containing 2.15 L of ethyl acetate and 8.60 L of hexane. The deposited precipitate was filtered, and washed with a hexane: ethyl acetate (3:1) solution, and then vacuum-dried. Lastly, the resulting precipitate was suspended in 1074 mL of anhydrous ethanol, and after having been stirred at 35° C. for 2 hours, the suspension was filtered and washed with anhydrous ethanol, and then vacuum-dried to obtain 45.39 g of one-terminal-methoxy polyethylene glycol-polyaspartic acid copolymer N-acetylated compound-doxorubicin condensation product. The rate of doxorubicin bonded to a side-chain carboxylic acid residue of a polyaspartic acid portion of the block copolymer was approximately 47%.

Production Example 7

To the one-terminal-methoxy polyethylene glycol-polyaspartic acid copolymer N-acetylated compound-doxorubicin condensation product (20.00 g) obtained in production example 6 was added 100 mL of injection-use water, and this was heated to 35° C., and suspended. To this was added 6.0 mL of a 0.5 N sodium hydroxide solution, and stirred, and then further added 100 mL of anhydrous ethanol. After it had been confirmed that the block copolymer was dissolved, 3.906 g of doxorubicin hydrochloride was added thereto, and dissolved therein. To this was added 5.9 mL of 0.5 N sodium hydroxide so as to adjust the pH to 6, and further added 188 mL of injection-use water. After a lapse of one hour, the solution was filtered by using a membrane filter (Millipore; GV type 0.22 μm), and the solvent was then distilled off under reduced pressure to obtain a solution of block copolymer-medicine complex, and this was frozen and dried to obtain 22.96 g of a freeze-dried matter of the block copolymer-medicine complex.

Example 1

The block copolymer (10.3 mg) obtained in production example 4 was dissolved in 10 mM acetic acid buffer solution (pH 7.0, 1 mL) to obtain 1.0043 g of a block copolymer solution. One portion (0.7491 g) of this solution was allowed to pass through a Sep-Pak QMA column (made by Waters Co., Ltd.) through which methanol, water and 10 mM acetic acid buffer solution (each having 5 mL) had permeated, and this was further washed with 10 mM acetic acid buffer solution (3 mL). The total 4.1171 g of solution including free-pass fractions and washing fractions was obtained. This solution was quantitatively determined through a high speed liquid chromatography having the following conditions, with a gel permeation column attached thereto. The quantity of polyethylene glycols contained therein was 0.1005 mg (1.3% by weight).
Column: Shodex OHpak SB803 +SB-G (made by Showa Denko K.K.)
Column temperature: 40° C.
Moving phase: 100 mM sodium chloride aqueous solution
Flow rate: 0.5 mL/min
Detector: differential refractometer detector
Injection amount: 50 μL Example 2

The block copolymer (10.3 mg) obtained in production example 4 was dissolved in 100 mM phosphoric acid buffer solution (pH 7.0, 1 mL) to obtain a block copolymer solution. This was allowed to pass through a Sep-Pak C18 column (made by Waters Co., Ltd.) through which methanol, water and 100 mM phosphoric acid buffer solution (each having 5 mL) had preliminarily passed, and this was further washed with 100 mM phosphoric acid buffer solution (3 mL). The total 4.1735 g of solution including free-pass fractions and washing fractions was obtained. This solution was quantity-measured through a high speed liquid chromatography having the following conditions, with a gel permeation column attached thereto. The quantity of polyaspartic acid contained therein was 0.250 mg (2.4% by weight).
Column: Asahipack GF310 HQ+Asahipak GF-1B (made by Asahi Kasei Corporation)
Column temperature: 40° C.
Moving phase: 100 mM phosphoric acid buffer solution (pH 7.0)
Flow rate: 0.5 mL/min
Detector: differential refractometer detector (or UV detector)
Injection amount: 50 μL Example 3

The one-terminal-methoxy polyethylene glycol-polyaspartic acid copolymer N-acetylated compound-doxorubicin condensation product (50 mg) obtained in production example 6 was precisely weighed, and dissolved in 25 mL of a 4% SDS:acetonitrile (1:1) solution. This solution was analyzed through a high speed liquid chromatography having the following conditions, and found to have isolated doxorubicin hydrochloride having a content of 1.29% by weight, and impurities derived from doxorubicin having a content of 0.15% by weight (as expressed in terms of doxorubicin hydrochloride equivalent on a basis of light absorbance).
Column: Capsule pack C18UG80 5 μm (made by Shiseido Co., Ltd.) i.d. 4.6 mm×150 mm
Column temperature: 40° C.
Moving phase: (A) 0.2% phosphoric acid, 0.15% SDS/$H_2O$: $CH_3CN$=7:3
(B) 0.2% phosphoric acid 0.15% SDS/$H_2O$:$CH_3CN$=3:7
Gradient: B % (minutes); 25 (0), 25 (13), 100 (30), 100 (40)
Flow rate: 1.0 mL/min
Detection: UV (254 nm)
Injection amount: 20 μL Example 4

The one-terminal-methoxy polyethylene glycol-polyaspartic acid copolymer N-acetylated compound-doxorubicin condensation product (30 mg), obtained in production example 6, was precisely weighed, and dissolved in 1 mL of dimethyl formamide. This solution was analyzed through a gas chromatography having the following conditions. The quantity of dicyclohexyl urea derivatives that were transferred and bonded was not more than 0.08% (not more than the detection limit).
Column: TC-1 (made by GL Science Co., Ltd.), 30 mm×0.25 mm i.d., film thickness 0.25 μm
Moving phase: Helium 0.8 mL/min
Column temperature: 70° C., 3° C./min, 88° C., 15° C./min, 180° C. (5 minutes)
Injection port: 290° C.
Detector: FID (290° C.)
Injection amount: Split (20:1), 1 μL Effects of the Invention The present invention makes it possible to provide a block copolymer having high purity from which polyethylene glycols and poly(acidic amino acids), contained in a block copolymer of polyethylene glycols and poly (acidic amino acid) as impurities, have been removed, to manufacture a polymeric carrier which is formed by condensing the copolymer and an anthracycline anticancer agent, and can be used for medical purpose as a carrier for a medicine and a gene, and also to provide a polymer pharmaceutical preparation that contains an anthracycline anticancer agent in an inner core of a micelle that is formed by the polymeric carrier.

It is clear that the impurities, which are contained in the block copolymer, and removed by the present invention, exert no functions for micelle formation and the like, and the polymeric carrier from which these have been removed is considered to exert superior functions. Moreover, the polymeric pharmaceutical preparation, obtained by using this high-purity polymeric carrier, is allowed to form a high-purity pharmaceutical preparation that is used for clinical purposes.

Moreover, the present invention also makes it possible to determine quantities of polyethylene glycols and poly(acidic amino acids) having carboxylic acid on its side chain which are impurities in the above mentioned block copolymer, and consequently to provide pieces of information that are useful in improving a manufacturing method of a block copolymer, planning production standards thereof and managing processes thereof.

What is claimed is:

1. A method for manufacturing a block copolymer of polyethylene glycols and poly(acidic amino acid), or a salt thereof, having a content of not more than 10% by weight impurities consisting of polyethylene glycols and poly(acidic amino acids) comprising:

refining polyethylene glycols by an ion exchange resin;

forming a block copolymer of the refined polyethylene glycols with poly(acidic amino acid);

removing a protective group, if present; and refining by a partition/adsorption resin.

2. The method according to claim 1, wherein the poly(acidic amino acid) is polyaspartic acid.

3. The method according to claim 1, wherein the block copolymer is a copolymer represented by formula (1):

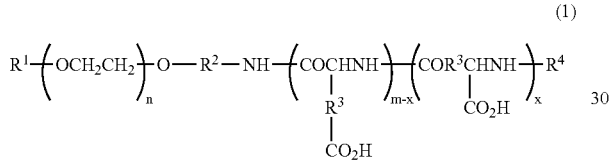

wherein, $R^1$ represents a hydrogen or lower alkyl group;

$R^2$ represents a bonding group;

$R^3$ represents a methylene or an ethylene group;

$R^4$ represents a hydrogen atom or a protective group of an amino group;

n is an integer of 5 to 1000;

m is an integer of 2 to 300;

x is an integer of 0 to 300; and x is not greater than m.

4. The method of claim 3, wherein, $R^1$ represents an alkyl group having 1 to 5 carbon atoms;

$R^2$ represents an alkylene group having 1 to 5 carbon atoms;

$R^3$ represents a methylene or an ethylene group;

$R^4$ represents a hydrogen atom or an acyl group having 1 to 5 carbon atoms;

n is an integer of 5 to 1000;

m is an integer of 2 to 300; and x is an integer of 0 to 300.

5. The method of claim 3, wherein, $R^1$ represents a methyl group;

$R^2$ represents a trimethylene group;

$R^3$ represents a methylene group;

$R^4$ represents an acetyl group;

n is an integer of 20 to 500;

m is an integer of 10 to 100; and x is an integer of 0 to 100.

* * * * *